US009801902B2

(12) United States Patent
Smith et al.

(10) Patent No.: US 9,801,902 B2
(45) Date of Patent: Oct. 31, 2017

(54) DEBRIDEMENT METHOD USING TOPICAL NITRIC OXIDE DONOR DEVICES AND COMPOSITIONS

(75) Inventors: Daniel J. Smith, Stow, OH (US); Patrick John Trotter, Leeds (GB); Mahesh Bhide, Akron, OH (US)

(73) Assignees: The University of Akron, Akron, OH (US); KCI USA, Inc., San Antonio, TX (US)

( * ) Notice: Subject to any disclaimer, the term of this patent is extended or adjusted under 35 U.S.C. 154(b) by 2512 days.

(21) Appl. No.: 12/087,837

(22) PCT Filed: Jan. 17, 2007

(86) PCT No.: PCT/US2007/001191
§ 371 (c)(1),
(2), (4) Date: Dec. 22, 2009

(87) PCT Pub. No.: WO2007/084533
PCT Pub. Date: Jul. 26, 2007

(65) Prior Publication Data
US 2011/0033437 A1     Feb. 10, 2011

Related U.S. Application Data (60) Provisional application No. 60/759,361, filed on Jan. 17, 2006, provisional application No. 60/763,724, filed on Jan. 31, 2006.

(51) Int. Cl.
*A61K 33/00* (2006.01)
*A61K 9/00* (2006.01)
*A61K 9/70* (2006.01)
*A61K 45/06* (2006.01)
*A61K 47/10* (2017.01)
*A61K 47/34* (2017.01)
(Continued)

(52) U.S. Cl.
CPC ............ *A61K 33/00* (2013.01); *A61K 9/0014* (2013.01); *A61K 9/7069* (2013.01); *A61K 45/06* (2013.01); *A61K 47/10* (2013.01); *A61K 47/34* (2013.01); *A61L 15/44* (2013.01); *A61L 26/0066* (2013.01); *A61L 2300/114* (2013.01)

(58) Field of Classification Search
CPC ..................................................... A61K 33/00
USPC ....................................................... 424/94.1
See application file for complete search history.

(56) References Cited

U.S. PATENT DOCUMENTS

4,043,331 A    8/1977  Martin et al.
4,878,908 A    11/1989 Martin et al.
6,382,526 B1   5/2002  Reneker et al.
(Continued)

*Primary Examiner* — Sharmila G. Landau
*Assistant Examiner* — Sheridan MaCauley
(74) *Attorney, Agent, or Firm* — Renner Kenner Greive Bobak Taylor & Weber (57) ABSTRACT

The present invention relates to methods for removal of dead tissue from wounds or skin using topical nitric oxide donor devices and/or compositions. In one embodiment, the present invention relates to a transdermal patch device that is designed to deliver nitric oxide. In another embodiment, the present invention relates to one or more devices and/or compositions that are designed to deliver nitric oxide and optionally one or more other compounds, where such devices/compositions include, without limitation, bandages, layered bandages, adhesive bandages, transdermal patches, creams, ointments, or a any combination of two or more thereof.

24 Claims, 6 Drawing Sheets (51) Int. Cl.
*A61L 15/44* (2006.01)
*A61L 26/00* (2006.01)

(56) References Cited

U.S. PATENT DOCUMENTS

| | | | |
|---|---|---|---|
| 6,520,425 B1 | 2/2003 | Reneker et al. | |
| 6,682,732 B1 * | 1/2004 | Blake et al. | 424/94.4 |
| 6,695,992 B2 | 2/2004 | Reneker | |
| 6,753,454 B1 | 6/2004 | Smith et al. | |
| 2002/0122771 A1 * | 9/2002 | Holland et al. | 424/43 |
| 2003/0165578 A1 | 9/2003 | Murrell | |
| 2005/0191372 A1 * | 9/2005 | Stenzler et al. | 424/718 |

* cited by examiner

DEBRIDEMENT METHOD USING TOPICAL NITRIC OXIDE DONOR DEVICES AND COMPOSITIONS

FIELD OF THE INVENTION

The present invention relates to methods for removal of dead tissue from wounds or skin using topical nitric oxide donor devices and/or compositions. In one embodiment, the present invention relates to a transdermal patch device that is designed to deliver nitric oxide. In another embodiment, the present invention relates to one or more devices and/or compositions that are designed to deliver nitric oxide and optionally one or more other compounds, where such devices/compositions include, without limitation, bandages, layered bandages, adhesive bandages, transdermal patches, creams, ointments, or a any combination of two or more thereof.

BACKGROUND OF THE INVENTION

As is known in the medical community, a need exists for a device and/or method to facilitate the easy removal of necrotic tissue from wounds such as diabetic ulcers. The process of doing so is known as debridement. Current forms of debridement include surgical, mechanical, autolytic, enzymatic and biological processes. Surgical debridement entails cutting away the necrotic tissue. Mechanical debridement involves using non-surgical mechanical methods to remove any dead tissue. For instance, one process involves applying saline-wetted gauze to the wound, allowing it to dry and then peeling away the gauze along with any adherent tissue. Surgical and mechanical procedures are often painful, and require some form of anesthetic.

Autolytic debridement entails allowing proteases naturally present in the patient to degrade the dead tissue. In contrast, enzymatic debridement involves adding proteases such as papain or collagenase to the wound to facilitate "removal" of the dead tissue. However, exogenous enzymes such as papain or collagenase attack both normal and necrotic tissues. Therefore, these enzymes must not be applied to healthy tissue. Finally, biological debridement involves using living organisms to remove necrotic tissue. For instance, one example of biological debridement involves applying maggots to a wound. Although this can be an effective means for debriding a wound, for obvious reasons most patients would find the procedure far too disagreeable.

Nitric oxide has been used in gaseous form to facilitate wound healing. For instance, devices exist that are gas chambers designed to conform to or surround a wound and apply gaseous nitric oxide thereto. This process has not been applied to wound debridement, but rather to stimulating the patient's tissues to facilitate healing, e.g., by increasing blood flow. Additionally, this process is cumbersome inasmuch as it requires connection to an external gas source and various fluidic parts. Furthermore, the process can incapacitate the patient when the treatment is applied to a foot, for instance.

Accordingly, there is a need in the art for debridement devices and methods that are both convenient to use and that cause less physical and psychological discomfort than the devices and/or methods currently utilized within the art.

SUMMARY OF THE INVENTION

The present invention relates to methods for removal of dead tissue from wounds or skin using topical nitric oxide donor devices and/or compositions. In one embodiment, the present invention relates to a transdermal patch device that is designed to deliver nitric oxide. In another embodiment, the present invention relates to one or more devices and/or compositions that are designed to deliver nitric oxide and optionally one or more other compounds, where such devices/compositions include, without limitation, bandages, layered bandages, adhesive bandages, transdermal patches, creams, ointments, or a any combination of two or more thereof.

In one embodiment, the present invention relates to a method for facilitating the removal of necrotic skin comprising: applying a nitric oxide-forming composition or device to a wound; dosing wound tissue with an effective amount of nitric oxide, wherein the nitric oxide loosens necrotic wound tissue; and removing the loosened necrotic wound tissue.

DETAILED DESCRIPTION OF THE PRESENT INVENTION

The present invention relates to methods for removal of dead tissue from wounds or skin using topical nitric oxide donor devices and/or compositions. In one embodiment, the present invention relates to a transdermal patch device that is designed to deliver nitric oxide. In another embodiment, the present invention relates to one or more devices and/or compositions that are designed to deliver nitric oxide and optionally one or more other compounds, where such devices/compositions include, without limitation, bandages, layered bandages, adhesive bandages, transdermal patches, creams, ointments, or a any combination of two or more thereof.

As used herein, the term "effective amount", as used to describe quantities of nitric oxide, includes amounts of nitric oxide that are capable of assisting in wound debridement. Without limitation, such assistance can take the form of loosening necrotic tissue and/or causing a visually perceptible changes in necrotic tissue.

As used herein, the term "absorbent polymer" includes any material capable of absorbing aqueous liquids, regardless of how the absorbent is made. Some examples of absorbent polymers within the scope of the present invention include, but are not limited to, cellulose, cellulose derivatives, pectins, starches, polyethyleneimine, polypropyleneimines, polybutyleneimines, polyurethanes, polyamides, and both linear and branched forms of each of the foregoing polymers. Additionally, absorbent polymers within the scope of the present invention include, but are not limited to, any copolymer of the foregoing polymers, and any combination thereof. For instance, acceptable absorbent polymers include any of the foregoing polymers grafted to an inert backbone, e.g. polyethyleneimine grafted to an otherwise relatively inert backbone such as a polysaccharide backbone, especially a cellulosic backbone. A non-limiting example of a material for forming an absorbent polymer in accordance with the present invention is high density linear polyethyleneimine (I-II) having a weight average molecular weight of greater than about 200,000.

The term "PLURONIC" is a trademark of BASF Corporation, Mount Olive, N.J. As used herein, the term "PLURONIC" includes high molecular weight polyoxyalkylene ethers having water soluble, surface active, and wetting properties.

The term "TECOPHILIC" is a trademark of Noveon IP Holdings Corporation, Cleveland, Ohio. As used herein, the term "TECOPHILIC" includes hydrophilic thermoplastic polyurethane compounds.

The term "DOWEX" is a trademark of Dow Chemical Company, Midland, Mich. As used herein, the term "DOWEX" includes all ion exchange resins sold under this trademark.

The term "nitric oxide releasing agent or compound" as used herein includes agents and/or compounds that release, generate and/or produce nitric oxide by some mechanism and/or chemical process.

Some embodiments of the present invention are directed to devices, preparations, and/or related methods for using nitric oxide-releasing compounds for wound debridement. More particularly, some embodiments of the present invention are directed to patches containing agents for nitric oxide delivery. Other embodiments of the present invention are directed to a variety of topical delivery systems such as creams. Some embodiments of the present invention are directed to methods of wound debridement using topical nitric oxide delivery systems, such as those taught herein. According to some embodiments of the present invention, such delivery systems can include a transdermal patch device.

Transdermal patch devices within the scope of the present invention generally comprise at least one fibrous component, which contains one or more compounds or agents that release and/or generate nitric oxide. In some embodiments of the present invention, the one or more compounds or agents that release, produce and/or generate nitric oxide are substantially inactive until contacted with a Bronsted acid known as an activating agent, which includes, but are not limited to, protic liquids such as water, physiological buffers, body fluids, saline and the like. Upon activation, the one or more compounds or agents that release and/or generate nitric oxide which diffuses into and through the skin. In some embodiments of the present invention, this above manner of producing nitric oxide can cause dead tissue to loosen and/or become readily removable. In some embodiments, the nitric oxide released, produced and/or generated by the devices of the present invention combines with dead tissue to form a visually identifiable raised region that can be readily removed.

Some embodiments of the present invention include one or more absorbent fibrous components that are relatively inert and/or do not produce nitric oxide. In some of these embodiments, the fibers of the one or more absorbent fibrous components can use their absorbency to hold, contain, absorb and/or wick liquids. Such embodiments can also use inert fibers to hold, contain and/or entrap one or more nitric oxide releasing agents or compounds, such as solid nitrites.

Figure 1:
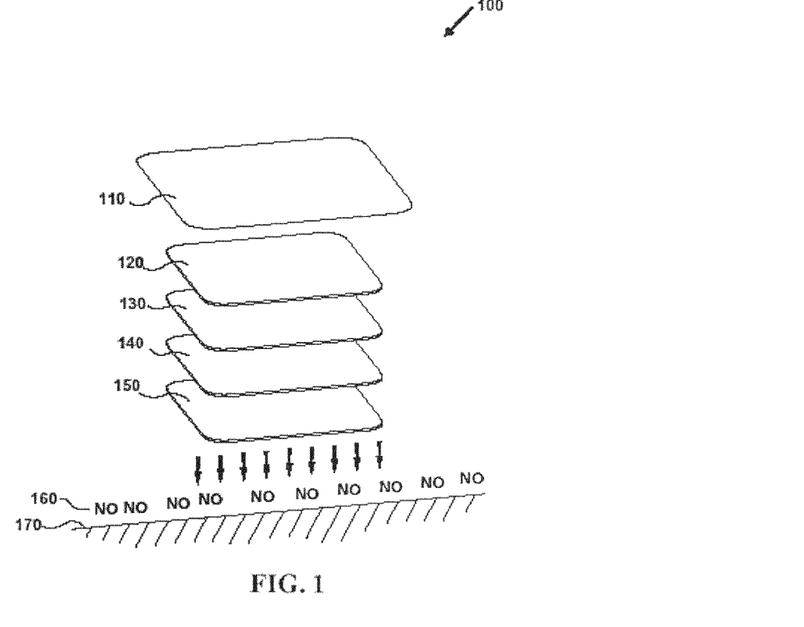
FIG. 1 is an illustration of a transdermal patch according to one embodiment of the present invention.

Turning to FIG. 1, one embodiment of the present invention comprises a patch device 100 having five layers a top layer 110, a second layer 120, a third layer 130, a fourth layer 140, and a fifth layer 150. In the embodiment of FIG. 1, top layer 110 comprises a backing component oriented to come into contact with, for example, a patient's skin. The backing component of top layer 110 can include, for example, an adhesive component for affixing the patch to the skin. As such, top layer 110 can be slightly larger than the remaining layers of patch device 100. Top layer 110 can also include a means for bonding other layers to the backing component of top layer 110. Suitable bonding means for attaching/bonding the remaining layers to top layer 110 include, but are not limited to, adhesives, stitching, adhesive tapes, or combinations of two or more thereof.

Second layer 120 of the patch can, in one embodiment, include a super-absorbent fibrous polymer layer. Third layer 130 can, in one embodiment, include a fibrous polymer, such as a polyurethane commercially available under the trade name TECOPHILIC®. The third layer 130 can also contain at least one activator (e.g., ascorbic acid). Additionally, a wide variety of protic weak acids can also be used as the one or more activators. Fourth layer 140 can be similar to, or the same as, second layer 120. Fifth layer 150, which is in direct contact with skin 170 can, in one embodiment, comprise fibrous hydrophilic polymers such as those commercially available under the trade names TECOPHILIC® and/or DOWEX®. According to this embodiment, the polymers making up fifth layer 150 can include, hold, contain and/or entrap at least one nitric oxide releasing/producing agent or compound such as one or more inorganic nitrite salts and/or one or more compounds that contain a suitable numbers of diazeniumdiolate moieties.

In one embodiment, patch device 100 can be inactive until activated by coming into contact with water and/or another aqueous-based fluid thereby causing the nitric oxide releasing/producing agent or compound to yield nitric oxide 160. Nitric oxide 160 can then diffuse through the skin 170 and assist in debridement and/or exfoliation in the vicinity of the patch.

In some embodiments, at least a portion of the fibrous components of a transdermal patch device can comprise a fiber capable of containing and/or comprising one or more nitric oxide-releasing agents. Fibers within the scope of the present invention include, without limitation, those which can reversibly react with nitric oxide to form functional groups, located on the fiber, comprising nitric oxide-releasing agent moieties. Other fibers can comprise those which can sequester or immobilize nitric oxide-releasing agents. More particularly, fibers that are suitable for derivatizing tend to contain secondary amine moieties inasmuch as secondary amines are known to react with nitric oxide to form diazeniumdiolates, which undergo a first order reaction evolving nitric oxide (Structures I and II).

(I) Polyethyleneimine (II) diazeniumdiolate

Acceptable nitric oxide-yielding fibrous components can comprise any fiberizable material having secondary amine moieties. More particularly, such components can comprise polymers including, but not limited to, polyethyleneimine, polypropyleneimines, polybutyleneimines, polyurethanes, polyamides, and both linear and branched forms of each of the foregoing polymers, and any suitable combination and/or copolymer thereof. Additionally, nitric oxide-yielding fibrous components can include any of the foregoing polymers grafted to an inert backbone, e.g., polyethyleneimine grafted to an otherwise relatively inert backbone such as a polysaccharide backbone, especially a cellulosic backbone. An example of a material for forming a fibrous component in accordance with the present invention comprises high density linear polyethyleneimine (e.g., Structures I and II) having a weight average molecular weight of greater than about 200,000. As is apparent to one of skill in the art, linear PEI is soluble in common solvents such as ethanol, but is insoluble in water.

Reacting PEI with nitric oxide ordinarily results in the formation of diazeniumdiolates, which causes the PEI to lose its solubility in ethanol, and in most cases become insoluble in water. When nitric oxide-modified PEI polymers are exposed to water they begin to decompose in predictable ways resulting in the release of nitric oxide. A typical nitric oxide release profile from a PEI fiber mat is generally short, with one to two days being a representative time.

Fibrous components that do not yield nitric oxide can include superabsorbent polymer materials. Suitable superabsorbent materials include, but are not limited to, one or more of polyethyleneimine, polypropyleneimines, polybutyleneimines, polyurethanes, polyamides, polylactic acid, polyethyleneglycol, cellulosic polymers, polysaccharides, or any suitable copolymer or combination thereof.

Fibrous components can be formed by any of a variety of known methods such as, without limitation, electrospinning and/or by a nanofibers by gas jet (NGJ) processes. Exemplary NGJ process, techniques and apparatuses are described in U.S. Pat. Nos. 6,382,526; 6,520,425; and 6,695,992, the disclosures of which are incorporated herein by reference in their entireties. Exemplary electrospinning processes and/or apparatuses are known from U.S. Pat. Nos. 4,043,331; 4,878,908; and 6,753,454, all of which are incorporated herein by reference in their entireties.

Briefly, the NGJ method comprises using a device having an inner tube and a coaxial outer tube with a sidearm. The inner tube is recessed from the edge of the outer tube thus creating a thin film-forming region. Polymer melt is fed in through the sidearm and fills the empty space between the inner tube and the outer tube. The polymer melt continues to flow toward the effluent end of the inner tube until it contacts the effluent gas jet. The gas jet impinging on the melt surface creates a thin film of polymer melt, which travels to the effluent end of tube where it is ejected forming a turbulent cloud of nanofibers.

It will also be appreciated by those of skill in the art that the above-mentioned fibrous components can be formed by methods other than electrospinning or NGJ. Any method of forming organic polymers into fibers known in the art can be used to form a fibrous component. For instance, extrusion methods such as wet spinning, dry spinning, melt spinning, and gel spinning are all acceptable methods of forming fibers in accordance with the present invention. Generally, finer denier fibers yield fiber mats having a greater surface area and thus more nitric oxide-releasing agents, which generally results in better performance. Accordingly, electrospinning and NGJ are especially effective methods for manufacturing the fibrous component.

In some embodiments a device according to the present invention can comprise a non-woven fibrous mat, or a layered non-woven fibrous mat. Additionally, the device can include one or more fibrous layers bounded by a membrane that selectively permits/allows nitric oxide to pass while being impervious to liquids such as activator solutions. However, the present invention need not include fibers at all. Accordingly, alternative embodiments can include, or are, a cream, gel, salve, ointment, balm, cerate, demulcent, liniment, lotion, lenitive, and/or unguent containing nitric oxide-releasing components. For instance, such embodiments can comprise a nitric oxide releasing agent or compound and an activating component that are mixed just prior to, or during, application.

According to some embodiments, a suitable nitric oxide releasing agent or compound can comprise any chemical entity that yields nitric oxide when stimulated to do so by an activator. It is appreciated in the art that such nitric oxide releasing agents or compounds can take several forms including, but not limited to, diazeniumdiolates. It is further appreciated in the art that nitric oxide releasing agents or compounds can take the form of o-alkylated diazeniumdiolate, or any o-derivatized diazeniumdiolate where the o-derivative can be converted back to the diazeniumdiolates. Such o-derivatized diazeniumdiolates are generally more stable than salts. Particularly, the energy of activation of the decomposition reaction is usually substantially higher than that of the non-o-derivatized form. Thus, the derivative tends to either not evolve nitric oxide in the absence of an enzymatic activator, or to extend the half-life of the diazeniumdiolate significantly. The non-o-derivatized diazeniumdiolate functional group, such as a salt, can comprise an effective nitric oxide releasing agent or compound, and is known to decompose by a first order mechanism in the presence of a proton source, i.e. activators.

Other nitric oxide releasing agents or compounds within the scope of the present invention include, but are not limited to, nitrites such as nitro-functionalized compounds. Representative compounds include nitroglycerine; N-(ethoxycarbonyl)-3-(4-morpholinyl)sydnoneimine; 3-morpholinosydnoneimine; 1,2,3,4-oxatriazolium 5-amino-3-(3,4-dichlorophenyl)-chloride; 1,2,3,4-oxatriazolium 5-amino-3-(chloro-2-methyl-phenyl)chloride; 1,2,3,4-oxatriazolium 3-(3-chloro-2-methylphenyl)-5-[[[cyanomethylamino]carbonyl]amino]-hydroxide inner salt; S-nitroso-N-acetyl-(D,L)-penicillamine; 1-[(4',5'-Bis(carboxymethoxy)-2'-nitrophenyl)methoxy]-2-oxo-3,3-diethyl-1-triazene dipotassium salt; and [1-(4',5'-bis(carboxymethoxy)-2'-nitropheyl)methoxy]-2-oxo-3,3-diethyl-1-triazine diacetoxymethyl ester.

Generally activators comprise any compound that stimulates the nitric oxide releasing agent or compound to produce nitric oxide. Where a diazeniumdiolate is the agent acceptable activators comprise proton sources, i.e. Bronsted acids. In general activators within the scope of the present invention include, but are not limited to, body fluids, alcohols, aqueous buffers, protic solvents, enzymes and catalysts. More particularly activators comprising body fluids include, but are not limited to, lymph, blood, and bile. Alcohol activators include, but are not limited to, methanol, ethanol, propanols, butanols, pentanols, hexanols, phenols, naphthols, and polyols. Activators comprising aqueous solutions include, but are not limited to, water, saline, phosphates, succinates, carbonates, acetates, formates, propionates, butyrates, fatty acids, amino acids, and ascorbic acids.

Methods of activating the nitric oxide releasing agent or compound of the present invention include, but are not limited to, contacting the nitric oxide releasing agent or compound with an activator. Further activation methods consistent with the present invention include, but are not limited to, photonic activation, wherein exposure to electromagnetic radiation stimulates a chemical reaction, which produces nitric oxide.

In one embodiment, the present invention comprises a process for using a non-woven nanofibrous mat derivatized with nitric oxide so as to form diazeniumdiolate moieties. The present invention, in this form, could be activated by applying the mat to an open wound, and allowing body fluids exuded by the wound to activate nitric oxide production. Another embodiment of the present invention comprises the foregoing wherein the mat comprises a component of an adhesive bandage.

Figure 2:
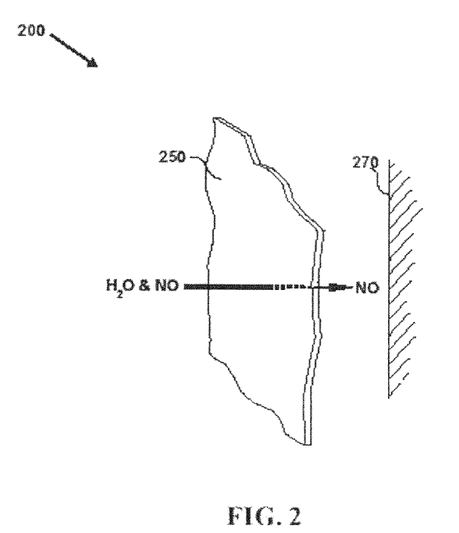
FIG. 2 is an illustration of a nitric oxide delivery device according to another embodiment of the present invention.
Figure 3:
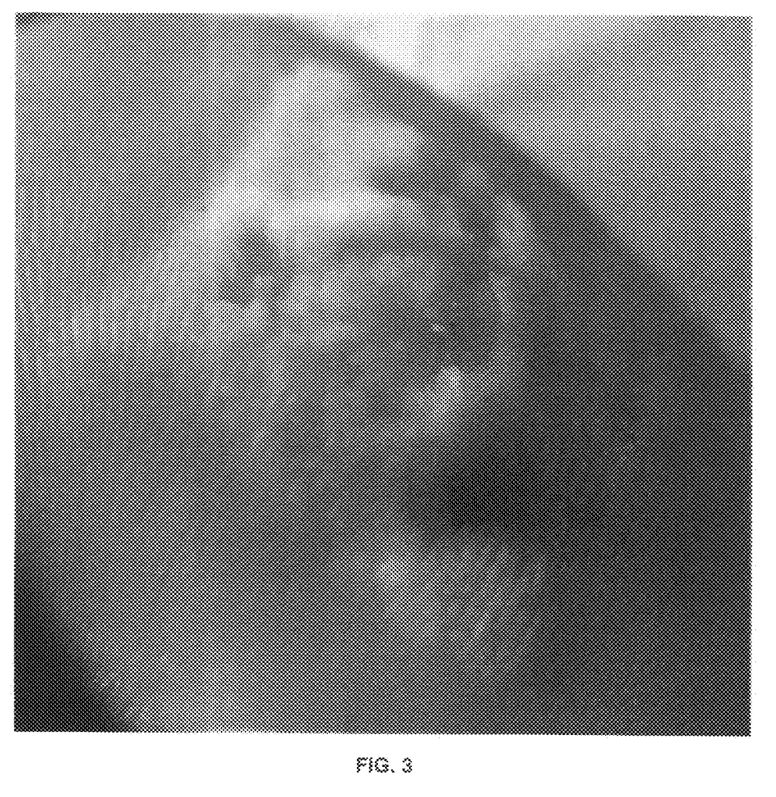
FIG. 3 is a photograph showing an area of previously necrotic skin that has been treated with a device in accordance with the present invention where the photograph illustrates that the necrotic skin has loosened and bears a distinctive raised appearance while the surrounding healthy skin remains relatively unaffected.
Figure 4:
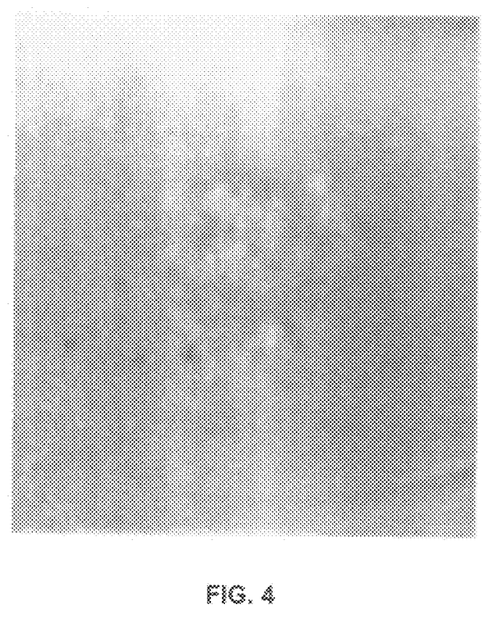
FIG. 4 is a photograph of a wart on the bottom of a foot.
Figure 5:
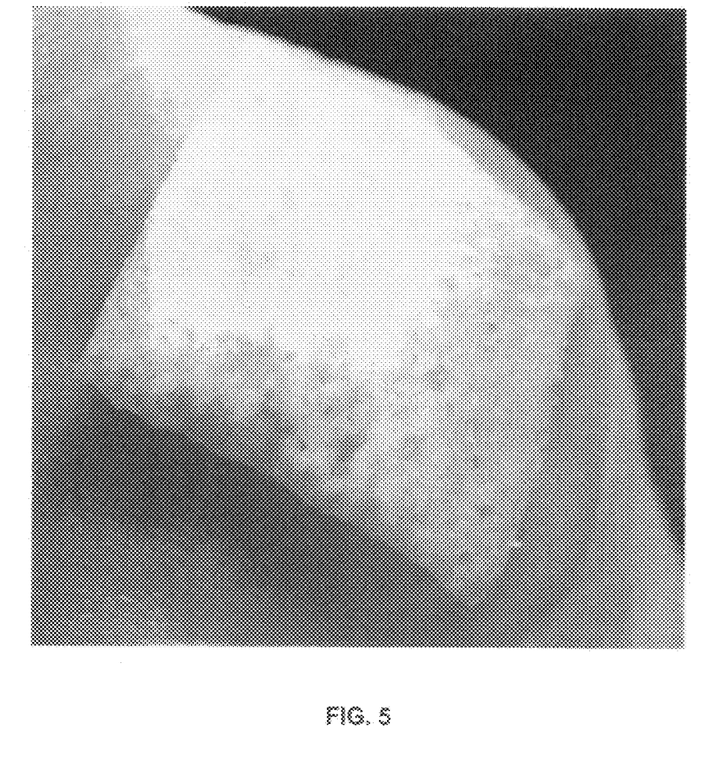
FIG. 5 is a photograph of a wart covered with a nitric oxide generating device in accordance with the present invention.
Figure 6:
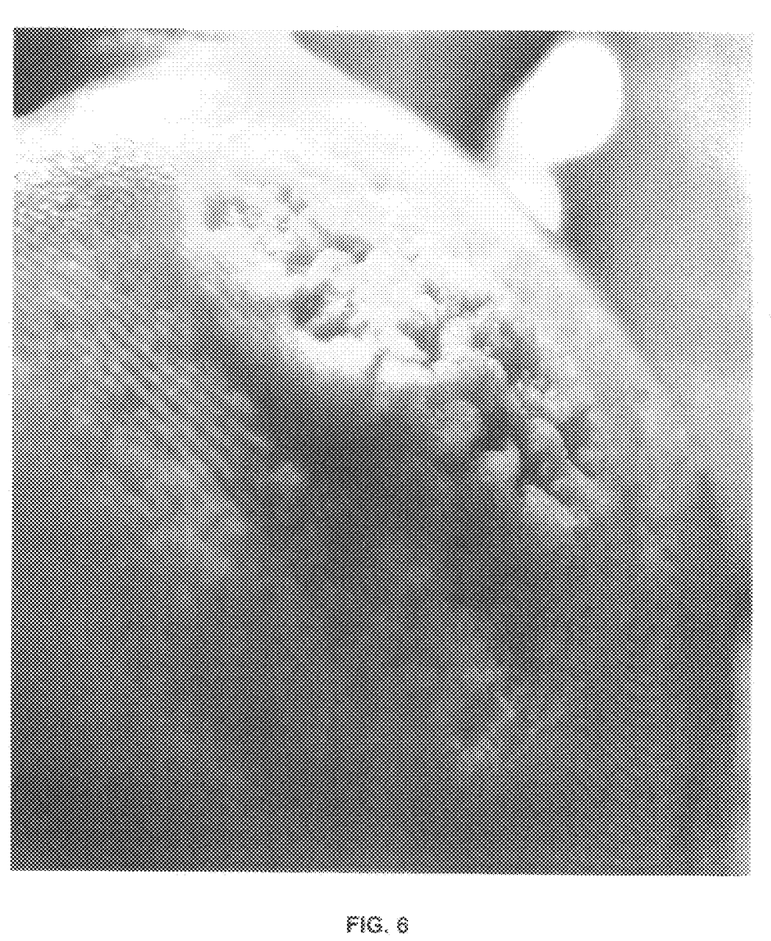
FIG. 6 is a photograph of treated skin showing that only the necrotic tissue is raised and/or loosened while healthy tissue remains relatively unaffected.

Another embodiment of the present invention can comprise multiple nanofibrous mat layers. For instance, one layer can comprise a nitric oxide-yielding fibrous material, while another layer comprises a fibrous material soaked in activator solution, wherein the two layers are separated by a barrier layer. The dressing is activated when the barrier layer is breached, for instance, by rupturing it. In an another embodiment, a device 200, as shown in FIG. 2, comprises a liquid barrier membrane 250 wherein membrane 250 contains therein at least one nitric oxide yielding, releasing and/or producing layer and at least one activator layer. Liquid barrier membrane 250 is, in one embodiment, designed to contain one or more portions that are permeable to nitric oxide.

As can be seen in FIG. 2, liquid barrier membrane 250 produces, yields and/or generates nitric oxide that is delivered to surface 270. Surface 270 can be, for example, skin.

Still another embodiment comprises a nitric oxide derivatized nanofiber electrospun directly onto a wound or other area where nitric oxide dosing would be beneficial. In this arrangement the fluids exuded by the wound can serve as the activator. Alternatively, an activator could be added to the mat after electrospinning.

In yet another embodiment, the present invention can include applying one or more antimicrobial components (i.e., medications) to the same wound or area being debrided. According to some embodiments such medications can be delivered as a component of a debridement preparation, such as a cream or ointment. Alternatively, such medications can be delivered as a component of a transdermal debridement patch. In still other embodiments, medications can be applied in addition to a patch or ointment. Antimicrobial agents within the scope of the present invention include, but are not limited to, iodine, silver, silver salts, cetylpyridinium chloride, clindamycin, metronidazole, chlorhexidine gluconate, doxycycline hyclate, triclosan, and minocycline. Additionally, the present invention can include additives such as growth factors, protease inhibitors, enzymes, and cofactors.

In some embodiments the present invention includes applying a nitric oxide releasing, generating and/or producing device or preparation to a wound. A device, such as a patch, can be wetted before, during and/or after application, thereby activating the patch. Alternatively, the patch may be applied dry and allowed to absorb body fluids which act to activate the patch. Furthermore, the device or preparation can deliver an amount of nitric oxide to the wound, which is effective to assist in debridement and/or exfoliation of the wound.

For example, in one embodiment, a nitric oxide derivatized polyethyleneimine patch is applied to a wound. The patch is left in contact with the wound for a dosing time between about 1 and about 100 hours, and delivers between from about 1 to about 1000µ mole/cm$^2$ of nitric oxide. Then the patch can be pulled from the wound along with a substantial portion of the loosened and/or dissolved necrotic tissue. The wound can then be washed and dressed accordingly. One of skill in the art would appreciate that this and other embodiments can be used alone or in combination with known debridement processes, devices and compositions.

In another embodiment, a nitric oxide-producing ointment preparation is applied to a wound. The preparation is left in contact with the wound for about 1 to about 100 hours, and delivers from about 1 to about 1000µ mole/cm$^2$ of nitric oxide. The wound can then be treated according to any of a wide variety of debridement or exfoliation procedures known in the art. The wound can then be washed and dressed accordingly. One of skill in the art will appreciate that this and other embodiments can be used alone or in combination with known debridement processes, devices and compositions.

Dosing times can be from about 1 to about 10 hours, from about 10 to about 20 hours, from about 20 to about 30 hours, from about 30 to about 40 hours, from about 40 to about 50 hours, from about 50 to about 60 hours, from about 60 to about 70 hours, from about 70 to about 80 hours, from about 80 to about 90 hours, or even from about 90 to about 100 hours. Here, as well as elsewhere in the specification and claims, individual range limits can be combined to yield additional and/or new ranges.

Dosages within the scope of the present invention include from about 1 to about 20µ mole/cm² of nitric oxide, from about 20 to about 30µ mole/cm² of nitric oxide, from about 30 to about 40µ Mole/cm² of nitric oxide, from about 40 to about 50µ mole/cm² of nitric oxide, from about 50 to about 60µ mole/cm² of nitric oxide, from about 60 to about 70µ mole/cm² of nitric oxide, from about 70 to about 80µ mole/cm² of nitric oxide, from about 80 to about 90µ mole/cm² of nitric oxide, from about 90 to about 100µ mole/cm² of nitric oxide, from about 100 to about 200µ mole/cm² of nitric oxide, from about 200 to about 300µ mole/cm² of nitric oxide, from about 300 to about 400µ mole/cm² of nitric oxide, from about 400 to about 500µ mole/cm² of nitric oxide, from about 500 to about 600µ mole/cm² of nitric oxide, from about 600 to about 700µ mole/cm² of nitric oxide, from about 700 to about 800µ mole/cm² of nitric oxide, from about 800 to about 900µ mole/cm² of nitric oxide, or even from about 900 to about 1000µ mole/cm² of nitric oxide.

In order to demonstrate the practice of the present invention, the following examples have been prepared. The examples should not, however, be viewed as limiting the scope of the invention.

EXAMPLES

Example 1

Formulation of a Topical Nitric Oxide Delivery Cream

In one embodiment, a first component is prepared by dissolving 3.0 grams of PLURONIC® polymer in 12 mL of ice cold water. Vitamin C (14 mg) is dissolved slowly in 3 mL of the ice cold PLURONIC® F-127 solution. The solution can be stored in a 5 cc disposable syringe. A second component is prepared by mixing 30 mg of ion exchange resin having nitric oxide-forming groups with 3 mL of ice cold PLURONIC® solution. This solution can be stored in a separate 5 cc disposable syringe. The compositions can be used by mixing the two reagents and applying the mixed ingredients to the wound.

Example 2

Preparation of 10µ molar Multilayer Electrospun Polymeric Transdermal Patch

In this example, a device of the present invention is fashioned from the following materials: hydrophilic (TECOPHILIC®) polymer solution (11.7%), nitric oxide-forming ion exchange resin (400 mesh size), microcrystalline stabilized vitamin C, an absorbent polymer, and absolute ethanol (200 proof).

In this example, fibers are electrospun using the following assembly: a metal cone (No. 2 with 1.5 mm opening) as a polymer solution reservoir, a metal collector for the collection of polymer fiber, and a 25 KV power supply. According to this example, the gap distance between the reservoir cone and metal collector is about 32 to 35 cm. However, one of skill in the art will recognize that the present invention is not limited to a gap distance within this range inasmuch as other gap distances will be appropriate depending on a variety of factors including variables related to the apparatus, electrospinning materials, conditions, and desired effects.

The bottom layer comes in contact with the skin, and like each of the other layers, it can be fabricated by electrospinning fibers from a solution. According to this example, a solution for fabricating the bottom layer comprises about 3.0 grams of nitric oxide-forming ion exchange resin, about 10.0 grams of TECOPHILIC® polymer solution, and about 4 to 5 mL of absolute ethanol. Furthermore, a solution for fabricating the second layer comprises about 1.5 grams of an absorbent polymer, about 10.0 grams of TECOPHILIC® polymer solution, and about 4 to 5 mL of absolute ethanol. A solution for fabricating the top layer comprises about 5.4 grams of microcrystalline stabilized vitamin C, about 10.0 grams TECOPHILIC® polymer solution, and about 5 to 6 mL of absolute ethanol. One of skill in the art will recognize that the present invention is not limited to the above preparations.

This example can be used by applying the patch to a wound and either wetting the patch with water, or allowing body fluids to enter the patch and thereby activate nitric oxide production.

Example 3

Preparation of 25µ molar Multilayer Electrospun Polymeric Transdermal Patch

In this example, the materials and electrospinning conditions are the same as set forth in Example 2. As in the previous example, the bottom layer contacts the wound, and is fabricated by electrospinning fibers from a solution. The bottom layer is fabricated from a solution comprising about 7.5 grams nitric oxide-forming ion exchange resin, about 10.0 grams of TECOPHILIC® polymer solution, and about 4 to 5 mL of absolute ethanol. A solution for fabricating the second layer comprises about 1.5 grams of an absorbent polymer, about 10.0 grams of TECOPHILIC® polymer solution, and about 4 to 5 mL of absolute ethanol. Finally, a solution for fabricating the top layer comprises about 7.0 grams of microcrystalline stabilized vitamin C, about 10.0 grams of TECOPHILIC® polymer solution, and about 5 to 6 mL of absolute ethanol. As in the previous example, this device can be used by either wetting it with water and applying it to the wound, or applying the dry patch to the wound and allowing body fluids to activate nitric oxide production.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A method for facilitating the removal of necrotic skin comprising: applying a nitric oxide-forming composition to necrotic tissue; activating the nitric oxide-forming composition such that it releases nitric oxide and doses the necrotic tissue with a dose of from about 1 to about 1000µ mole/cm² of nitric oxide, wherein the nitric oxide loosens the necrotic tissue; and removing the loosened necrotic tissue.

2. The method of claim 1, wherein the nitric oxide-forming composition is provided in a bandage, transdermal patch, or a cream.

3. The method of claim 1, wherein the step of activating further comprises dosing with nitric oxide in an amount from about 1 to about 100µ mole/cm².

4. The method of claim 1, wherein the step of activating further comprises dosing with nitric oxide in an amount from about 100 to about 200μ mole/cm$^2$.

5. The method of claim 1, wherein the step of activating further comprises dosing with nitric oxide in an amount from about 200 to about 300μ mole/cm$^2$.

6. The method of claim 1, wherein the step of activating further comprises dosing with nitric oxide in an amount from about 300 to about 400μ mole/cm$^2$.

7. The method of claim 1, wherein the step of activating further comprises dosing with nitric oxide in an amount from about 400 to about 500μ mole/cm$^2$.

8. The method of claim 1, wherein the step of activating further comprises dosing with nitric oxide in an amount from about 500 to about 600μ mole/cm$^2$.

9. The method of claim 1, wherein the step of activating further comprises dosing with nitric oxide in an amount from about 600 to about 700μ mole/cm$^2$.

10. The method of claim 1, wherein the step of activating further comprises dosing with nitric oxide in an amount from about 800 to about 900μ mole/cm$^2$.

11. The method of claim 1, wherein the step of activating further comprises dosing with nitric oxide in an amount from about 900 to about 1000μ mole/cm$^2$.

12. The method of claim 1, wherein the effective amount of nitric oxide is delivered in from about 1 to about 100 hours.

13. The method of claim 1, wherein the step of removing further comprises surgically, mechanically, or enzymatically removing necrotic tissue, or any combination thereof.

14. The method of claim 1, further comprising the step of applying an antimicrobial component.

15. The method of claim 14, wherein the antimicrobial component comprises one or more of iodine, silver, silver salts, cetylpyridinium chloride, clindamycin, metronidazole, chlorhexidine gluconate, doxycycline hyclate, triclosan, or minocycline.

16. The method of claim 1, further comprising at least one additive.

17. The method of claim 16, wherein the at least one additive comprises one or more of at least one growth factor, protease inhibitor, enzyme, or cofactor.

18. The method of claim 1, wherein the nitric oxide forming composition comprises at least one nitric oxide releasing agent and at least one activator.

19. The method of claim 18, wherein the at least one nitric oxide releasing agent comprises diazeniumdiolate.

20. The method of claim 18, wherein the at least one activator comprises one or more of at least one body fluid, alcohol, aqueous buffer, protic solvent, enzyme or catalyst.

21. The method of claim 20, wherein the at least one body fluid comprises one or more of lymph, blood, or bile.

22. The method of claim 20, wherein the at least one alcohol comprises one or more of methanol, ethanol, propanol, butanol, pentanol, hexanol, phenol, naphthol, polyol, and the like.

23. The method of claim 20, wherein the at least one aqueous buffer comprises one or more of water, saline, phosphate, succinate, carbonate, acetate, formate, propionate, butyrate, fatty acid, amino acid, or ascorbic acid.

24. The method of claim 1, wherein the necrotic tissue is a wart.

* * * * *